(12) United States Patent
Esteve

(10) Patent No.: US 12,042,599 B2
(45) Date of Patent: Jul. 23, 2024

(54) DRY POWDER INHALER

(71) Applicant: EMPHASYS IMPORTADORA EXPORTADORA E DISTRIBUIDORA LTDA., Porto Feliz (BR)

(72) Inventor: Victor Esteve, Itú (BR)

(73) Assignee: EMPHASYS IMPORTADORA EXPORTADORA E DISTRIBUIDORA LTDA., Porto Feliz (BR)

( * ) Notice: Subject to any disclaimer, the term of this patent is extended or adjusted under 35 U.S.C. 154(b) by 895 days.

(21) Appl. No.: 17/040,081

(22) PCT Filed: Mar. 13, 2019

(86) PCT No.: PCT/IB2019/000174
§ 371 (c)(1),
(2) Date: Sep. 22, 2020

(87) PCT Pub. No.: WO2019/202383
PCT Pub. Date: Oct. 24, 2019

(65) Prior Publication Data
US 2021/0016024 A1   Jan. 21, 2021

(30) Foreign Application Priority Data

Apr. 16, 2018   (DE) .................. 10 2018 108 958.9

(51) Int. Cl.
*A61M 15/00*   (2006.01)

(52) U.S. Cl.
CPC .... *A61M 15/0041* (2014.02); *A61M 15/0003* (2014.02); *A61M 15/0023* (2014.02);
(Continued)

(58) Field of Classification Search
CPC .............. A61M 15/0041; A61M 15/00; A61M 15/0003; A61M 15/0023; A61M 15/0035;
(Continued)

(56) References Cited

U.S. PATENT DOCUMENTS 2,549,303 A * 4/1951 Friden ................... A61M 15/00
128/203.15
4,852,561 A * 8/1989 Sperry ............... A61M 15/0086
128/200.23
(Continued)

FOREIGN PATENT DOCUMENTS

EP          3009364 B1    4/2016
KR      20070011466 A    1/2007
(Continued)

OTHER PUBLICATIONS

International Search Report and Written Opinion Form PCT/IS/210 and PCT/ISA/237, International Application No. PCT/IB2019/000174, pp. 1-9, International Filing Date Mar. 13, 2019, mailing date of search report May 29, 2019.
(Continued)

*Primary Examiner* — Michael R Reid
*Assistant Examiner* — Tyler A Raubenstraw
(74) *Attorney, Agent, or Firm* — BOND, SCHOENECK & KING, PLLC; George R. McGuire

(57) ABSTRACT

A dry powder inhaler for at least two capsules containing dry powder is provided, the dry powder inhaler including: At least two capsule chambers, each capsule chamber for receiving one of the capsules; a mouth piece with a mouth portion comprising a distal opening; and a duct structure between the distal opening of the mouth piece and the at least two capsule chambers, wherein the duct structure comprises at least two primary ducts, wherein the distal opening of the mouth piece leads into the at least two (Continued)

primary ducts, and wherein each one of the at least two primary ducts leads into the corresponding one of the at least two capsule chambers.

13 Claims, 6 Drawing Sheets

(52) U.S. Cl.
CPC .... *A61M 15/0035* (2014.02); *A61M 15/0086* (2013.01); *A61M 2202/064* (2013.01); *A61M 2206/16* (2013.01)

(58) Field of Classification Search
CPC ........ A61M 15/0086; A61M 2202/064; A61M 2206/16
See application file for complete search history.

(56) References Cited

U.S. PATENT DOCUMENTS

| | | | |
|---|---|---|---|
| 5,002,048 A | 3/1991 | Makiej | |
| 7,931,022 B2* | 4/2011 | Johnson | A61P 25/04 128/203.15 |
| 9,700,690 B2* | 7/2017 | Poole | A61M 15/0093 |
| 2003/0075172 A1* | 4/2003 | Johnson | A61P 19/02 424/46 |
| 2005/0268908 A1* | 12/2005 | Bonney | A61M 15/0051 128/203.15 |
| 2007/0181124 A1* | 8/2007 | Casper | A61P 25/00 128/200.24 |
| 2009/0064996 A1* | 3/2009 | Rosh | A61M 15/0003 128/200.23 |
| 2009/0216183 A1* | 8/2009 | Minotti | B05B 11/1081 604/82 |
| 2012/0055467 A1* | 3/2012 | Brambilla | B65D 83/682 128/200.21 |
| 2012/0145150 A1 | 6/2012 | Donovan et al. | |
| 2016/0045685 A1* | 2/2016 | Hyde | A61M 15/008 128/200.14 |
| 2016/0158470 A1* | 6/2016 | Esteve | A61M 15/0041 128/203.15 |
| 2017/0071505 A1* | 3/2017 | Stenzler | A61M 15/002 |
| 2017/0304563 A1* | 10/2017 | Adelson | A61M 15/003 |
| 2017/0340003 A1* | 11/2017 | Batista | A24F 40/46 |
| 2018/0207377 A1* | 7/2018 | Buehler | A61M 15/0035 |
| 2018/0289904 A1* | 10/2018 | Ellwanger | A61M 15/0028 |
| 2020/0360631 A1* | 11/2020 | Li | A61M 15/003 |

FOREIGN PATENT DOCUMENTS

| | | |
|---|---|---|
| WO | 03035137 A2 | 5/2003 |
| WO | 2004052435 A1 | 6/2004 |
| WO | 2015006838 A1 | 1/2015 |

OTHER PUBLICATIONS

Translated Korean Office Action, App. No. KR20067023534A, published Jan. 24, 2007, pp. 1-10, dated Sep. 25, 2023.

\* cited by examiner

DRY POWDER INHALER

CROSS-REFERENCE TO RELATED APPLICATION

The present application is the United States National Phase application of PCT Application PCT/IB2019/000174 filed Mar. 13, 2019, which relates and claims priority to German Application No. 10 2018 108 958.9 filed Apr. 16, 2018, the entirety of each of which is incorporated herein by reference.

BACKGROUND OF THE INVENTION

The present invention relates to a dry powder inhaler.

WO2015006838 discloses a powder inhaler, consisting of a base housing, snap-in capsule receptacle mounted together with a lid; a moveable mouthpiece with cap and guided by lateral stems and vertical guide; a perforation device for opening the capsule; a flow guide tube, centralized and housed in the mouthpiece and on the guide; a de-agglomeration chamber formed above the housing of the capsule; a vertical passage formed between said de-agglomeration chamber and the upper edge of the mouthpiece; an air intake point positioned between the walls of the capsule receptacle and the base housing which in turn has one or two air intake points with a pocket and include one or more secondary air flow passages.

In view of this, an object of the present invention is to provide an improved dry powder inhaler.

SUMMARY OF THE INVENTION

A dry powder inhaler for at least two capsules containing dry powder is provided. The dry powder inhaler comprises: At least two capsule chambers, each capsule chamber for receiving one of the capsules; a mouth piece with a mouth portion comprising a distal opening; and a duct structure between the distal opening of the mouth piece and the at least two capsule chambers, wherein the duct structure comprises at least two primary ducts, wherein the distal opening of the mouth piece leads into the at least two primary ducts, and wherein each one of the at least two primary ducts leads into the corresponding one of the at least two capsule chambers.

Advantageously, each one of the at least two capsule chambers accommodates a capsule, which releases its powder, when the patient sucks/inhales via the mouth piece. Therefore, the drug mass delivered to the lungs is increased as the at least two capsules solve their drug components into the air. So, the efficiency of drug mass delivery is increased.

The inhaler has the following advantages, one is to deliver higher dose mass efficiently in terms of fine particle fraction because single capsule chamber inhalers while dose mass is increased out of one capsule, the result from de-agglomeration and resulting fine particle dose (particles under 4.6 microns, percentage of the powder which effectively reach the lower lung part) is not proportional. That is, while increasing the dose mass out of one capsule there is a tendency that fine particle fraction on the delivered dose is reduced. Therefore, it is preferable to deliver separate and simultaneous doses securing a high fine particle fraction. Delivering high dose mass from single capsules is used for the treatment diseases which requires for example antibiotic therapy which dose mass is frequently high to reach a therapeutic dose. Also the inhaler advantageously allows to deliver two separate active substances for lung therapy, often drugs are therapeutically complementary, need to be delivered simultaneously, but are not chemically stable together. Therefore the inhaler allows loading one different drug in each chamber for combined delivery, often the case of corticoid and bronchodilator drugs used for treatment of asthma and Chronic Obstructive Pulmonary Disease (COPD).

Moreover, two different drugs in corresponding capsules can be inserted into the capsule chambers in order to deliver a mixture of the two drugs via one inhalation to the lungs of the patient. Especially in the case, where two drug formulations are chemically not stable, the dry powder inhaler provides a solution.

In addition, the at least two capsule chambers remember the patient to insert at least two capsules instead of only a first one and forget the second one. The inhaler prevents that the patient forgets the application of the prescribed drug application in form of at least two capsules.

Moreover, the explained advantages are reached with an economic constructive inhaler, reduced number of components and assembly steps.

According to an example the duct structure is Y-shaped, wherein the duct structure comprises a secondary duct between the distal opening of the mouth piece and the at least two primary ducts. Advantageously, the Y-shape of the duct structure provides a junction arranged towards the distal opening of the mouth piece. The junction provides that the at least two primary drug-air-mixtures originating from the capsule chambers are mixed into a secondary drug-air mixture.

According to an example the secondary duct comprises a secondary cross-sectional area, which equals or is less than a sum of primary cross-sectional areas of the at least two primary ducts. Advantageously, this provides that the velocity of the drug-air mixture in the secondary duct is equal or greater than the velocity of the drug-air mixtures in the primary ducts.

According to an example the length of the secondary duct is equal or greater than the length of one of the primary ducts. The longer the length of the secondary duct the higher the velocity of the drug-air mixture stream is and lapse for substances flushed together in the air stream from the two chambers to mix each other during inhalation for reaching the lungs.

According to an example the mouth piece comprises the Y-shaped part of the duct structure. For inserting dry powder capsules the Y-shaped part of the duct is facing away together with the mouth piece from openings of the capsule chambers.

Consequently, further components for establishing the Y-shaped duct part of the duct structure are not necessary. So, collocating the Y-shaped part of the duct structure into the mouth piece establishes a reduced complexity of the inhaler and offers an increased ease of use for the patient.

According to an example the two primary ducts enclose an angle between 30° and 60°. Advantageously, this angle range provides that the drug-air mixtures of the at least two primary ducts is mixed properly.

According to an example a sharp edge is arranged between the at least two primary ducts. The flow of the drug-air mixtures originating from the capsule chambers is advantageously not interfered by air drag but can easily pass the junction at the sharp edge. Moreover, the sharp edge increases the generation of vortexes in flow direction. Therefore, the mixture leaving the mouth piece is mixed more homogeneously.

According to an example the dry powder inhaler comprises an actuator button movable relative to the at least two capsule chambers from a normal position to a perforation position along an actuation direction, and wherein perforation needles attached to the actuator button extend into each one of the at least two capsule chambers when the actuator button is moved into the perforation position. Advantageously, the patient operates the dry powder inhaler easily by pushing the actuator button for inhaling both drugs of the capsules.

According to an example each capsule chamber comprises a retaining section for retaining the respective capsule when being pierced, wherein the at least two retaining sections have the same orientation.

According to an example the retaining sections extend perpendicular to the actuation direction of the actuator button. The perpendicular orientation of the retaining section allows that the actuator button is arranged closer to the retaining sections. This allows a smaller construction of the whole dry powder inhaler.

According to an example each capsule chamber comprises a rotating section, wherein each one of the rotating sections confines at least partly a cylindrically-shaped interior space. This shape enables a rotational movement of the capsules in order to ameliorate the turbulences for producing the air-drug-mixture.

According to an example the rotating sections define a common rotational plane perpendicular to a longitudinal axis of the inhaler for both capsules. This common rotational plane reduces space in terms of height of the dry powder inhaler. Moreover, the air-drug-mixture is advantageously homogenized.

According to an example two first openings in a casing of the dry powder inhaler, each leading into a different one of the at least two capsule chambers, are arranged adjacent to each other on one side of the inhaler, and wherein two second openings in the casing of the dry powder inhaler, which lead into the different capsule chambers, are facing away from each other the opposite side of the inhaler. This provides a construction of the inhaler, where the two first openings can be arranged, where the user will probably not tap the first openings with his hands. Advantageously this ensures the functioning of the inhaler and increases usability.

According to an example the two first openings are arranged on the side comprising the actuator button. This provides that the first openings being arranged closely to each other are not covered by the patients hands or fingers as the attention of the patient is to press the actuator button. As can be noticed, with this position of air intakes both capsules while inhalation rotate: one clock wise, the other anti-clock wise. Both capsules rotate together.

BRIEF DESCRIPTION OF THE DRAWINGS

More features and advantages are described in relation to the figures.

DETAILED DESCRIPTION

Figure 1:
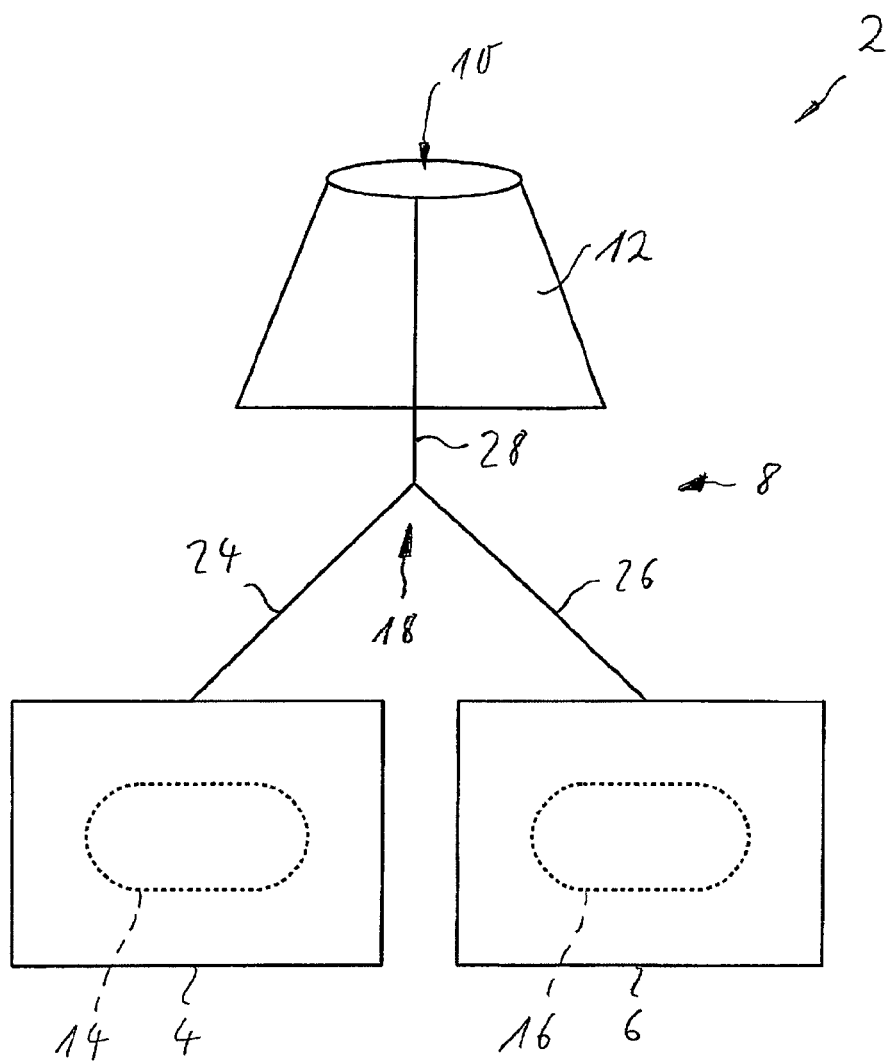
FIG. 1 depicts a schematic view of a dry powder inhaler.

FIG. 1 depicts a schematic view of a dry powder inhaler 2. The dry powder inhaler 2 comprises at least two capsule chambers 4, 6, each capsule chamber 4, 6 is configured to receive one capsule 14, 16. A duct structure 8 is arranged between a distal opening 10 of a mouth piece 12 and the at least two capsule chambers 4, 6. The duct structure 8 has a shape of an Y. The duct structure 8 comprises at least two primary ducts 24 and 26, wherein each one of the at least two primary ducts 24 and 26 connects the corresponding capsule chamber 4, 6 with a junction 18. In the area of the junction 18 the at least two primary ducts 24 and 26 merge into a secondary duct 28 leading to the distal opening 10. In summary, the duct structure 8 connects the distal opening 10 with openings of the capsule chambers 4, 6.

Figure 2:
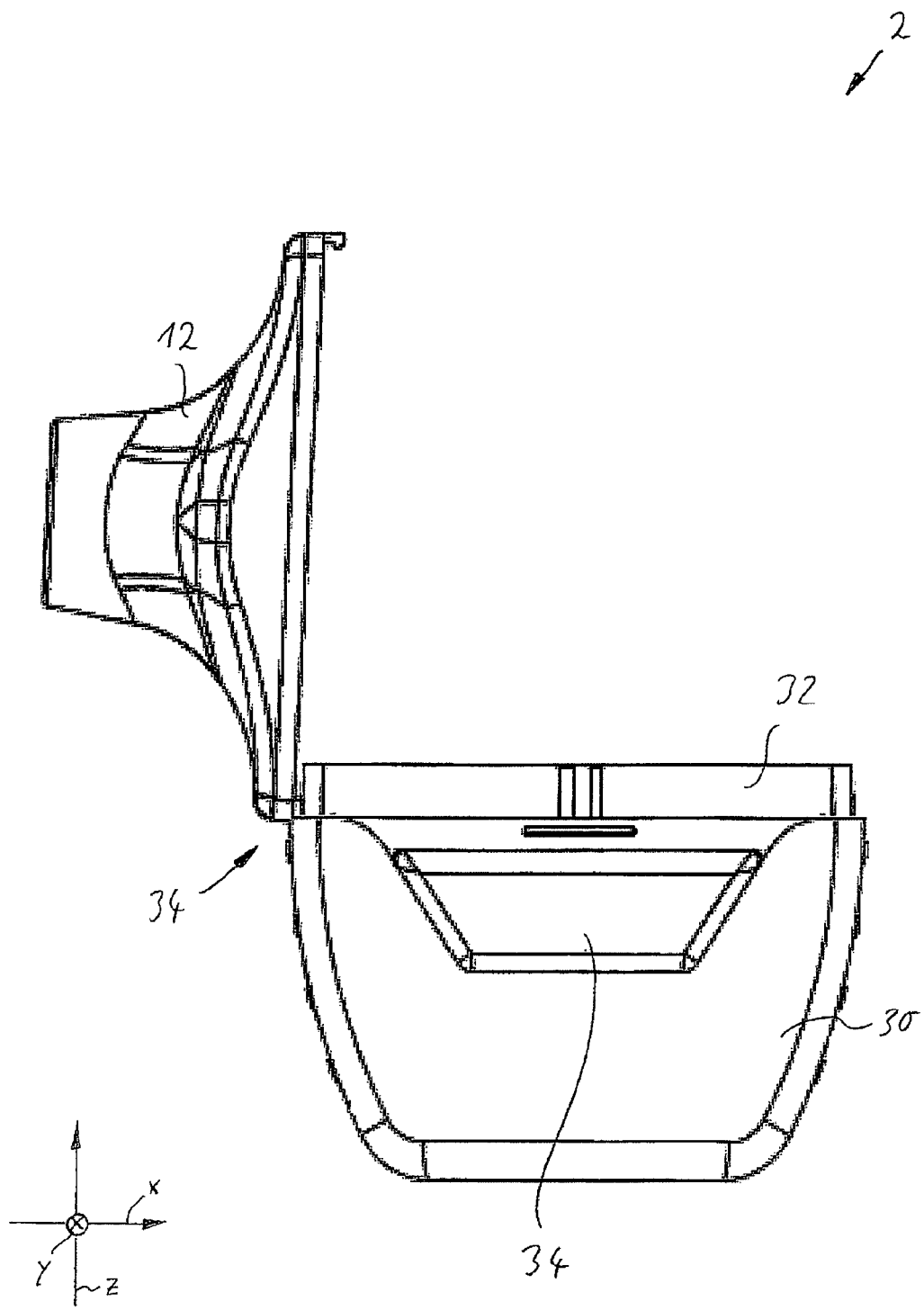
FIG. 2 depicts a side view of the inhaler.

FIG. 2 shows a side view of the inhaler 2. A bottom covering body 30 retains a capsule chamber piece 32, which comprise the at least two capsule chambers, and an actuator button 34. The mouth piece 12 is arranged at the capsule chamber piece 32 via a hinge 36.

Figure 3:
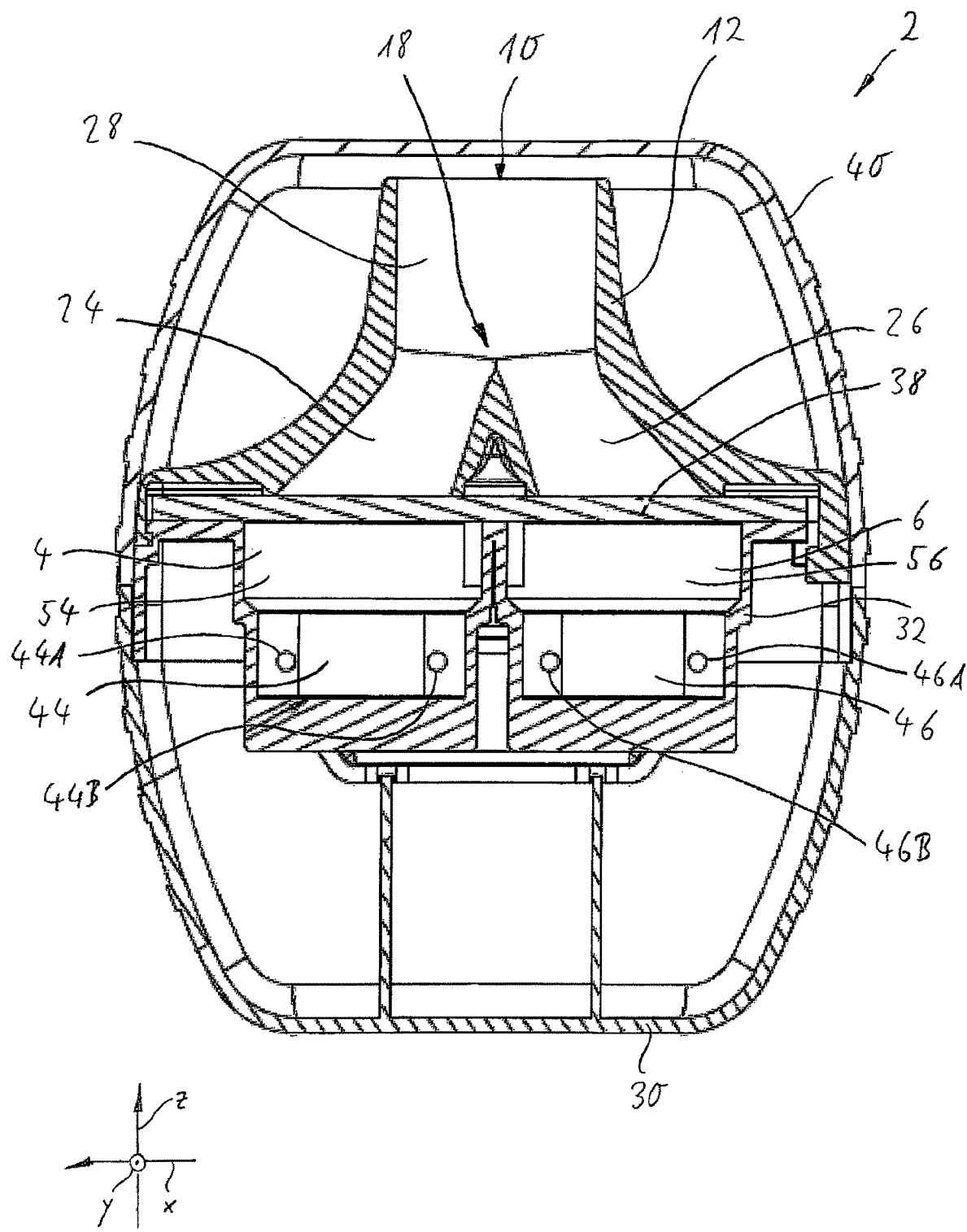
FIG. 3 depicts a schematic sectional view of the dry powder inhaler.

FIG. 3 depicts a schematic sectional view of the dry powder inhaler 2. The capsule chamber piece 32 comprises the capsule chambers 4 and 6, wherein each capsule chamber 4, 6 comprises a corresponding retaining section 44 and 46 for retaining the capsules when being inserted, and a corresponding rotating section 54 and 56 for rotating the capsule after being pierced in the retaining section 44, 46. The retaining section 44 comprises two passageways 44A and 44B for accommodating perforation needles. The retaining section 46 comprises two passageways 46A and 46B for accommodating perforation needles.

Both capsule chambers 4 and 6 have the same structure. When air is sucked via the mouth piece 12, the pierced capsules elevate from the respective retaining section 44, 46 into the corresponding rotating section 54, 56. Each of the rotating sections 54 and 56 confines at least partly a cylindrically-shaped interior space, that enables the rotation of the capsules in an imaginary rotation plane perpendicular to a longitudinal axis of the secondary duct 28 and/or perpendicular to a longitudinal axis of the inhaler 2. Both cylinder axes of the rotating sections 54 and 56 are parallel to each other. The rotating section 54, 56 define the common rotation plane.

The openings of the capsule chambers 4, 6 are covered by a mesh piece 38, which comprises passageway openings connecting the capsule chamber 4, 6 with the corresponding one of the primary ducts 24, 26. The mesh piece 38 is connected to the mouth piece 12. In inhaling direction z the two primary ducts 24, 26 lead into the common secondary duct 28. The mouthpiece 12 is covered by a covering body 40.

The mouth piece 12 comprises a main body, which comprises the inner Y-shaped duct structure 8, and the mesh piece 28. As the mouth piece 12 is arranged at the capsule chamber piece 32 via a hinge 36, the mouth piece 12 can therefore be removed from the openings of both the capsule chambers 4, 6. The mouth piece 12 thus releases the openings of both the capsule chambers 4, 6 to insert or remove the plurality of capsules. On the other hand, if the mouthpiece 12 closes the capsule chambers 4, 6 of the capsule chamber piece 32, the mesh piece 28 prevents particles originating from the destroyed capsules from entering the duct structure 8 and being inhaled during inhalation.

Figure 4:
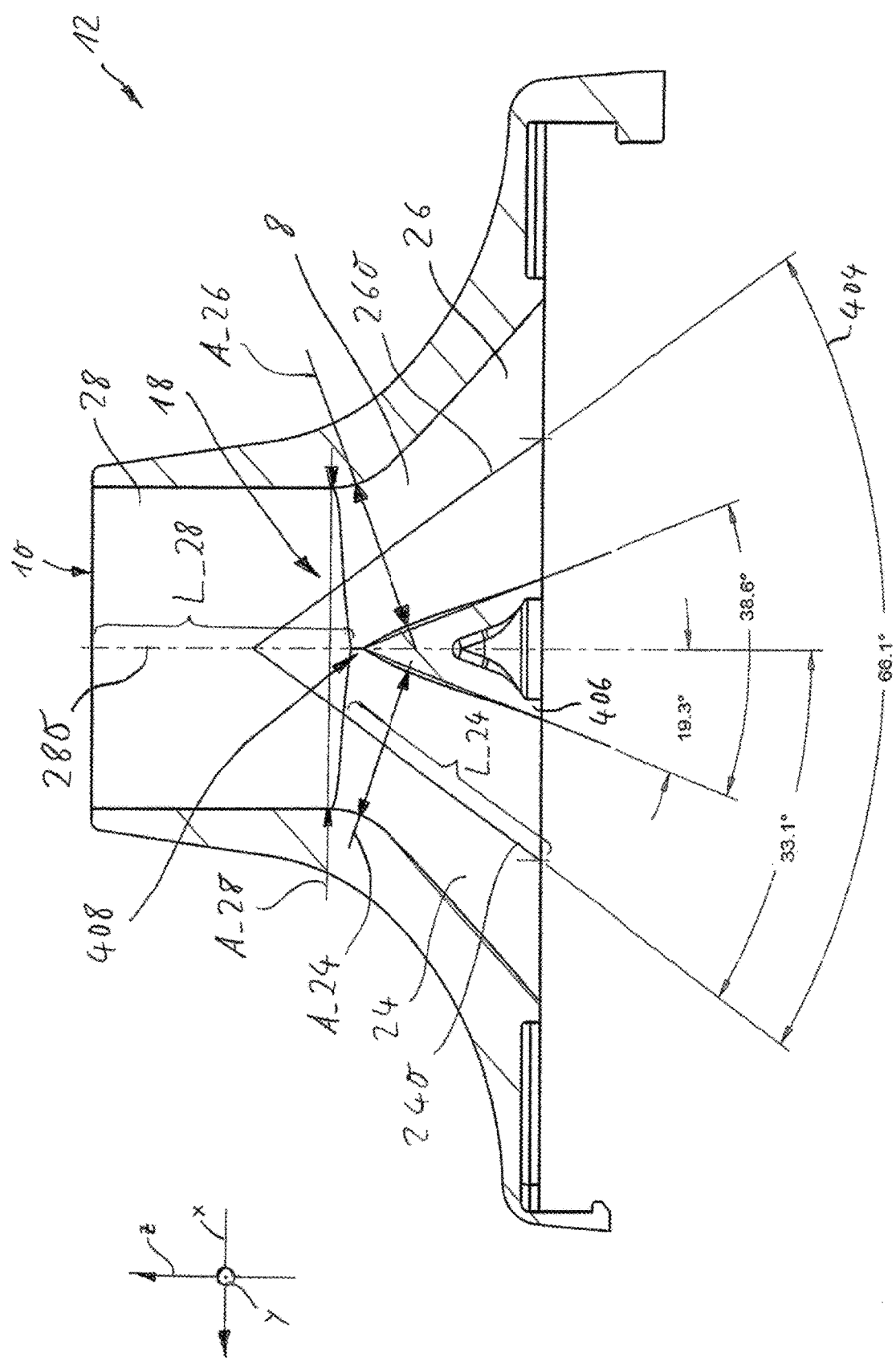
FIG. 4 depicts a schematic sectional view of a mouth piece.

FIG. 4 depicts a schematic sectional view of the mouth-piece 12 comprising the Y-shaped duct structure 8. The secondary duct 28 comprises a length L_28 which is equal or greater than a length L_24 of one of the primary ducts 24, 26. The secondary duct 28 comprises a smallest secondary cross-sectional area A_28. The primary duct 26 comprises a smallest secondary cross-sectional area A_26. The primary duct 28 comprises a smallest secondary cross-sectional area A_28. The secondary area A_28 equals or is less than a sum of all the primary areas A_28 and A_26.

The longitudinal axis 280 of the secondary duct 28 extends parallel to the axis z. A longitudinal axis 240 of the primary duct 24 and a longitudinal axis 260 of the primary duct 26 enclose and angle 404 of 66.1°. A central portion 406 of the mouth piece leads in direction z into a sharp edge 408, which is arranged between the two primary ducts 24, 26. The sharp edge 408 has a radius of less than 1 mm, especially below 0.5 mm, especially below 0.25 mm, and especially below 0.1 mm, wherein the radius is perpendicular to a longitudinal axis of the sharp edge 408.

Figure 5:
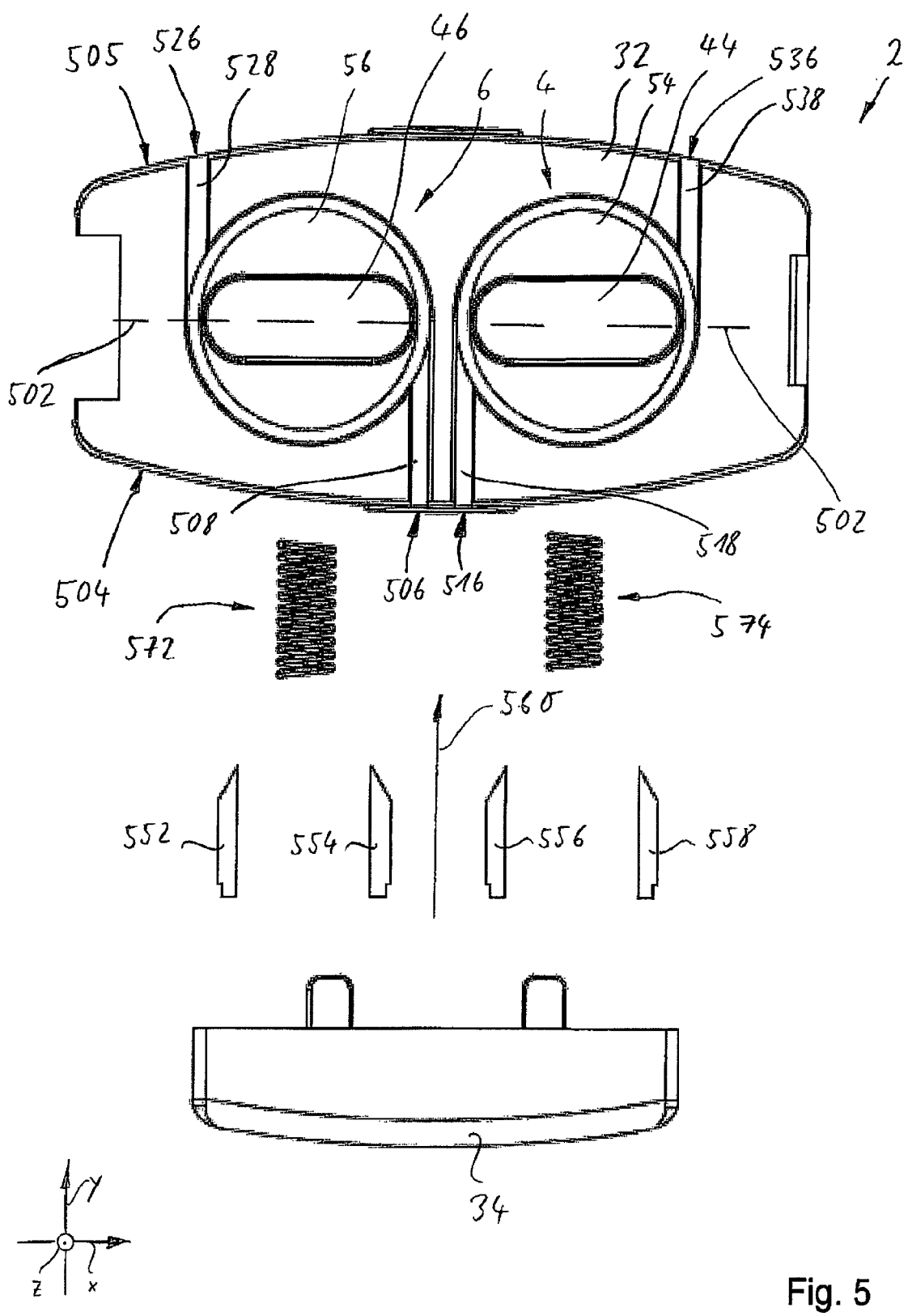
FIG. 5 depicts a schematic exploded view of a capsule chamber piece.

FIG. 5 depicts a schematic exploded view of the capsule chamber piece 32 and actuator button 34. The retaining sections 44 and 46 comprise a common longitudinal axis 502. In direction z the retaining section 44, 46 opens into the corresponding rotating section 54, 56.

Passageways 508, 518 connect first openings 506, 516 on a first side 504 of the inhaler 2 with the corresponding but different one of the capsule chambers 6, 4. Passageways 528, 538 connect second openings 526, 536 on a second side 505 with the corresponding but different one of the capsule chambers 6, 4. The first and the second side 504 and 505 are opposed to each other and face away from each other. This results in the first capsule rotating clock-wise, and the second capsule rotating anti-clock-wise. Of course, in another example the passageways 508 and 518 are arranged so that the rotation directions of the capsules are the same.

Perforation needles 552 to 558 are connected to the actuator button 34. The actuator button 34 is movable from the normal position to a perforation position along an actuation direction 560, which is parallel to the axis y and perpendicular to the axis 502. In the perforation position the perforation needles 552 to 558 enter the corresponding retaining section 44 and 46 to pierce the capsules arranged therein. After piercing the capsules springs 572 and 574 push the actuator button 34 into the normal position.

The form of the retaining sections 44 and 46 follow the common longitudinal axis 502 in order to enable the simultaneous piercing by pushing the actuator button 34. The axis 502 is perpendicular to a longitudinal axis of the inhaler 2.

After the perforation of the capsules both capsules will rotate inside the corresponding rotating section 54, 56. The rotational movement of the capsules happens in a common imaginary plane, which is parallel to the plane of projection, and which is perpendicular to the longitudinal axis 280 of the secondary duct 28 shown in FIG. 4.

Figure 6:
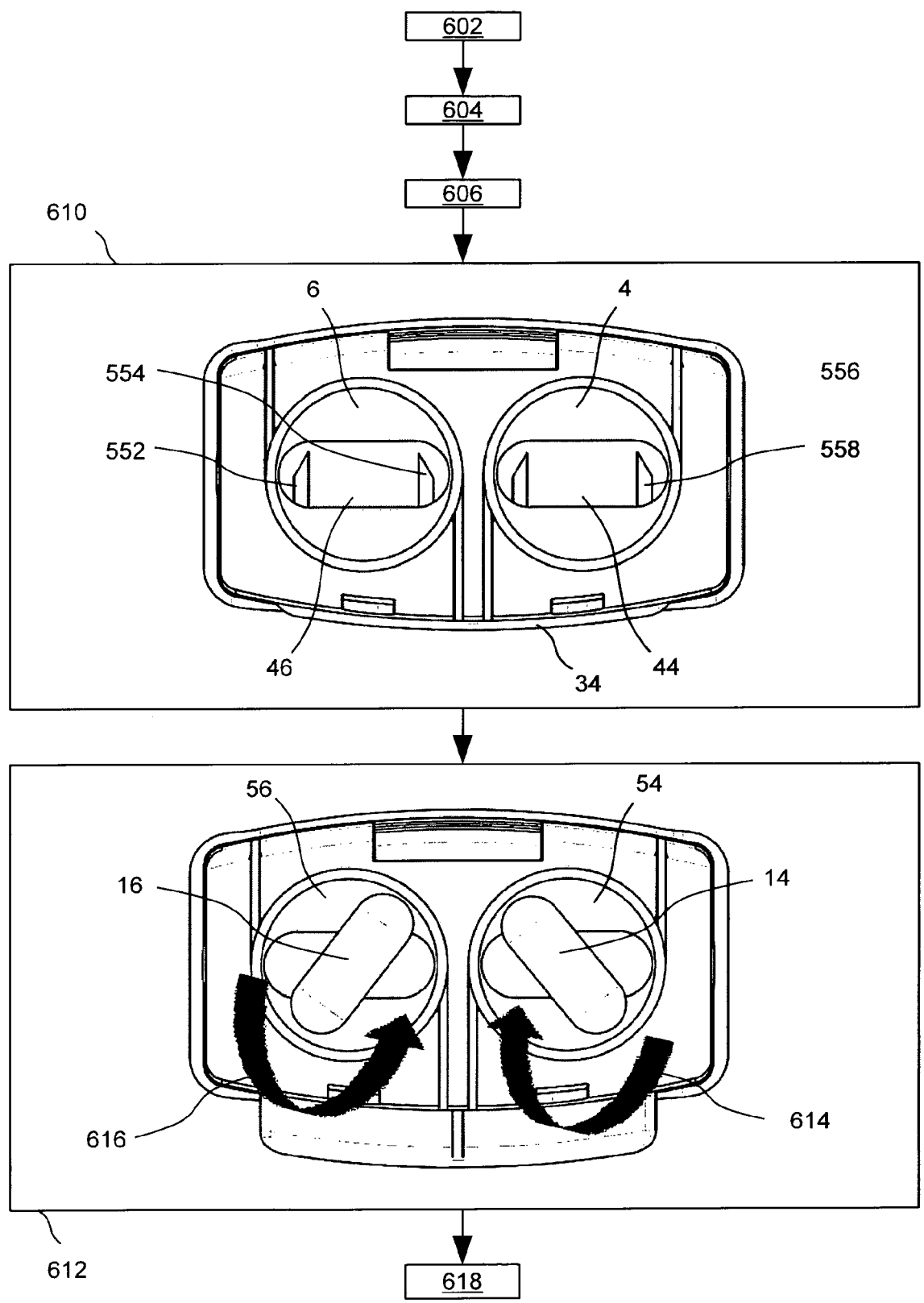
FIG. 6 shows a schematic flow diagram for using the dry powder inhaler 2.

FIG. 6 shows a schematic flow diagram for using the dry powder inhaler 2. According to a step 602 the user opens the dry powder inhaler 2 by retracting the mouth piece 12 from the capsule chamber piece 32. After conducting the step 602, the mouth piece 12 gives access to the capsule chambers 4, 6.

According to a step 604 the user inserts two capsules into the corresponding one of the retaining sections 44, 46 of the dry powder inhaler 2. If the inhaler 2 is held so that the retaining sections 44, 46 are oriented downwards, the capsules remain in the retaining sections 44, 46. According to a step 606 the mouth piece 12 is returned to the closed position back to the capsule chamber piece 32 in order to close both capsule chambers 4, 6.

According to a step 610 the user presses the actuator button 34, so that the needles 552-558 enter simultaneously both of the retaining sections 44, 26. First the respective capsule 14, 16 moves by inserting the needles 552-558 in the direction of a wall of the respective retaining section 44 and 46, the wall facing away from the button 34, in order to then break through a shell of the respective capsule 14, 16 at its distal ends. The button 34 is released again in step 610 after opening capsules 14 and 16 and returns to its unpressed position. For reasons of a clear view, the capsules 14, 16 in step 310 are not shown.

When step 610 is completed, the user can use inhaler 2 in step 612 by airtightly enclosing the distal opening 10 of inhaler 2 with his mouth and subsequent inhaling. Inhalation creates a negative pressure in duct structure 8, which passes this negative pressure on to the capsule chambers 4 and 6. This reduced pressure lifts the capsules 14, 16 from the retaining section 44, 46 to the rotating section 54, 56. Each rotating section 54, 56 defines a hollow cylindrical space that allows rotation according to arrows 614 and 616. The capsules 14 and 16 rotate in opposite directions to each other due to the air flow described above to FIG. 5. Through the distal openings of capsules 14 and 16 created in step 610, the drug emerges from capsules 14 and 16 into the rotating sections 54 and 56 where it mixes with incoming air. The rotating capsules 14 and 16 are prevented from penetrating into structure 8 by the sieve-like mesh piece 38. The drug-air-mixture produced in the rotating section 54, 56 is then passed through duct structure 26 to the distal end of mouth piece 12 and inhaled by the user. Therefore, the rotating sections 54 and 56 provide a first and second mixing stage producing two drug-air-mixtures. The duct structure 8 provides with its junction a third mixing stage for mixing the two drug-air-mixtures originating from the rotating sections 54 and 56. The junction 18 and therefore also the third mixing stage is arranged between the distal opening 10 of the mouth piece 12 and the capsule chambers 4 and 6. By using different drugs in the capsules 14 and 16 the three mixing stages provide taking up two different drugs with one inhalation procedure.

Once the drug-air-mixture has been inhaled, the user opens inhaler 2 in step 618 and removes the emptied capsules 14 and 16 for disposal.

The invention claimed is:

1. A dry powder inhaler for at least two capsules containing dry powder, the dry powder inhaler comprising:
   at least two capsule chambers, each capsule chamber for receiving one of the capsules;
   a mouth piece extending along a longitudinal axis and with a mouth portion comprising a distal opening and a one-piece main body, which comprises a duct structure; and
   the duct structure of the mouth piece arranged along the longitudinal axis of the mouth piece between the distal opening of the mouth piece and the at least two capsule chambers, wherein the duct structure comprises at least two primary ducts, wherein the distal opening of the mouth piece leads into the at least two primary ducts, and wherein each one of the at least two primary ducts leads into the corresponding one of the at least two capsule chambers,
   wherein two first openings in a casing of the dry powder inhaler, each leading into a different one of the at least two capsule chambers, are arranged adjacent to each other on one side of the inhaler, wherein the dry powder inhaler comprises an actuator button movable relative to the at least two capsule chambers from a normal position to a perforation position along an actuation direction, wherein the two first openings are arranged on the side comprising the actuator button.

2. The dry powder inhaler according to claim 1, wherein the duct structure is Y-shaped, and wherein the duct structure comprises a secondary duct between the distal opening of the mouth piece and the at least two primary ducts.

3. The dry powder inhaler according to claim 2, wherein the secondary duct comprises a secondary cross-sectional area, which equals or is less than a sum of primary cross-sectional areas of the at least two primary ducts.

4. The dry powder inhaler according to claim 2, wherein the length of the secondary duct is equal or greater than the length of one of the primary ducts.

5. The dry powder inhaler according to claim 1, wherein the mouth piece comprises the Y-shaped part of the duct structure.

6. The dry powder inhaler according to claim 1, wherein the two primary ducts enclose an angle between 30° and 60°.

7. The dry powder inhaler according to claim 1, wherein a sharp edge is arranged between the at least two primary ducts.

8. The dry powder inhaler according to claim 1 wherein perforation needles attached to the actuator button extend into each one of the at least two capsule chambers when the actuator button is moved into the perforation position.

9. The dry powder inhaler according to claim 1, wherein each capsule chamber comprises a retaining section for retaining the respective capsule when being pierced, wherein the at least two retaining sections have the same orientation.

10. The dry powder inhaler according to claim 8, wherein the retaining sections extend perpendicular to the actuation direction of the actuator button.

11. The dry powder inhaler according to claim 1, wherein each capsule chamber comprises a rotating section, wherein each one of the rotating sections confines at least partly a cylindrically-shaped interior space.

12. The dry powder inhaler according to claim 11, wherein the rotating sections define a common rotation plane perpendicular to a longitudinal axis of the inhaler.

13. The dry powder inhaler according to claim 1, wherein two second openings in the casing of the dry powder inhaler, which lead into the different capsule chambers, are facing away from each other the opposite side of the inhaler.

* * * * *